United States Patent [19]

Storr

[11] Patent Number: 4,718,270

[45] Date of Patent: Jan. 12, 1988

[54] POROSIMETER AND METHODS OF ASSESSING POROSITY

[75] Inventor: Bernard Storr, Kent, United Kingdom

[73] Assignee: Coulter Electronics, Ltd., Luton, England

[21] Appl. No.: 694,555

[22] PCT Filed: May 17, 1984

[86] PCT No.: PCT/GB84/00170

§ 371 Date: Jan. 17, 1985

§ 102(e) Date: Jan. 17, 1985

[87] PCT Pub. No.: WO84/04593

PCT Pub. Date: Nov. 22, 1984

[30] Foreign Application Priority Data

May 17, 1983 [GB] United Kingdom ............... 8313635

[51] Int. Cl.⁴ .......................................... G01N 15/08
[52] U.S. Cl. .......................................................... 73/38
[58] Field of Search ................................................ 73/38

[56] References Cited

U.S. PATENT DOCUMENTS

| 2,842,958 | 7/1958 | Sayre, Jr. et al. | 73/38 |
|---|---|---|---|
| 3,991,605 | 11/1976 | Reuland | 73/38 |
| 4,191,046 | 3/1980 | Baker et al. | 73/38 |
| 4,198,853 | 4/1980 | Graham et al. | 73/38 |
| 4,198,854 | 4/1980 | Washington et al. | 73/38 |
| 4,213,327 | 7/1980 | Prescott, Jr. et al. | 73/38 |
| 4,424,707 | 1/1984 | Pezzi | 73/38 |
| 4,480,463 | 11/1984 | Schumacher et al. | 73/38 |
| 4,506,542 | 3/1985 | Rose | 73/38 |

FOREIGN PATENT DOCUMENTS

| 0064159A | 11/1982 | European Pat. Off. |
| 1063832 | 8/1959 | Fed. Rep. of Germany . |
| 0779399 | 7/1957 | United Kingdom . |
| 1219776 | 1/1971 | United Kingdom . |
| 2018436A | 10/1979 | United Kingdom . |
| 2095411A | 9/1982 | United Kingdom . |

OTHER PUBLICATIONS

W. Fischer et al. "Eine Methode zur Ermittlung der Porengrobenverteilung" from Messtechnik 12/68, pp. 309–313, Jun. 24, 1968.

3M, "Fluorinert® Electronic Liquids", 1982 Edition.

ASTM F316-80, "Standard Test Method for Pore Size Characteristics of Membrane Filters for Use with Aerospace Fluids", pp. 298–304.

Primary Examiner—Stewart J. Levy
Assistant Examiner—Hezron E. Williams
Attorney, Agent, or Firm—Gerald R. Hibnick

[57] ABSTRACT

A porosimeter comprises a gas supply, a gas pressure regulator for the gas supply, a sample holder having an inlet and an outlet, said inlet being connected to the gas pressure regulator, a gas pressure sensor connected to the gas pressure regulator for measuring the pressure of gas supplied to the sample holder, and a gas flow sensor wherein the gas flow sensor is disposed to measure the gas flow between said gas pressure regulator and said sample holder. Both pressure and flow-rate readings are taken directly from the respective sensors to an automatic recorder which draws mechanically the output in the form of a graph, or may feed them to, for example, an integrating computer.

15 Claims, 3 Drawing Figures

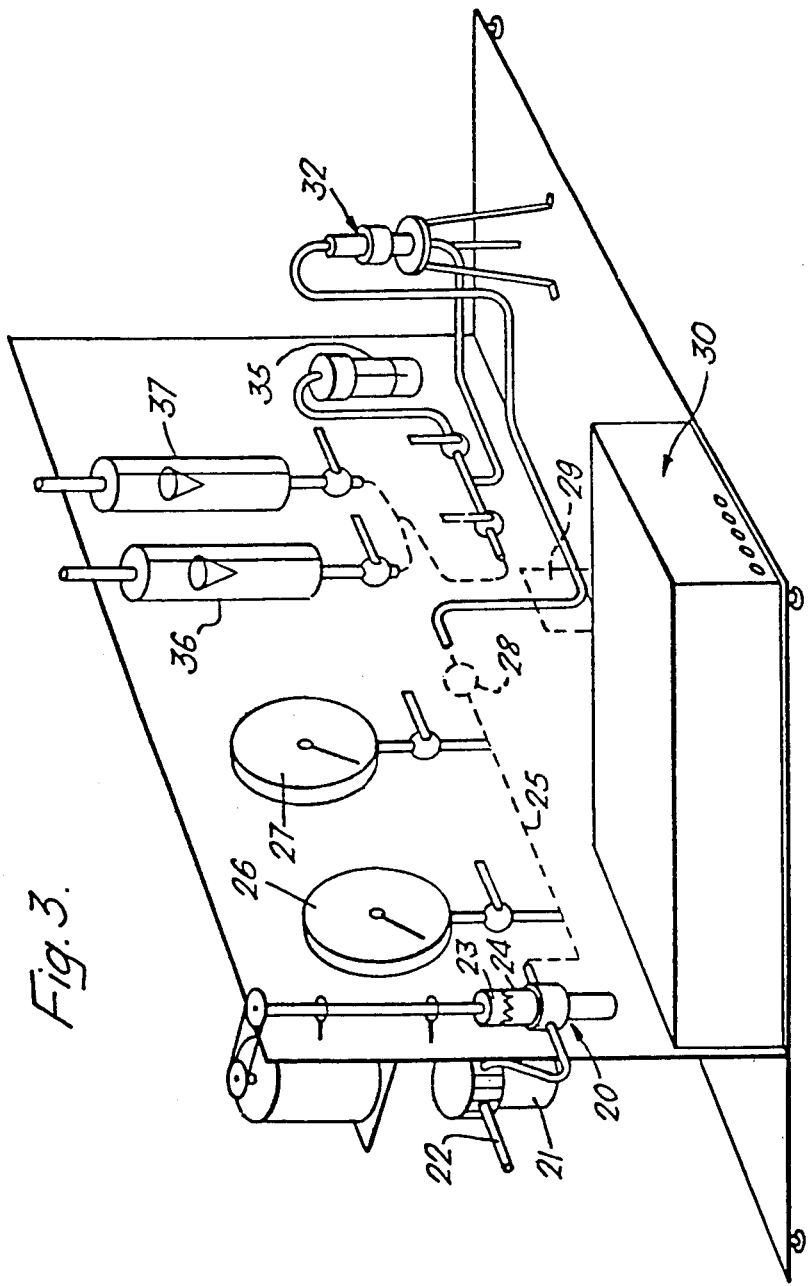

POROSIMETER AND METHODS OF ASSESSING POROSITY

BACKGROUND OF THE INVENTION

This invention relates to porosimeters and to methods of assessing pore size characteristics, such as pore size distribution.

A widely accepted standard apparatus and method for testing assessing pore size is to be seen in ASTM F 316-80 by the American Society for Testing and Materials.

According to such apparatus and method, the material is saturated with test liquid, held in a holder and subjected to progressively increasing pressure of a test gas. The initial breakthrough of gas through the wet filter is noted by a bubble point detector and thereafter the relationship between pressure applied and flow through the material is observed using a pressure gauge and a rotameter downstream of the material and directly impelled by the flow of gas. Such prior art test method is highly dependent on the manual skill and dexterity and the intellectual ability of the operator requiring as it does the simultaneous operation of the inlet pressure regulator and observation of the pressure gauge and the flow rate. Thereafter these readings have to be converted manually by drawing graphs and these are then interpreted. Despite these drawbacks this method is one of the accepted methods of testing porosity.

SUMMARY OF THE INVENTION

I have examined this prior art and have in the present invention provided substantial improvements in various respects and in particular from the point of view of avoiding reliance upon manual skill. The object of this invention is to gain information about the maximum pore size and the distribution of pore sizes in a porous material under test.

In my apparatus and method I use a pressure gauge and flow meter only in an initial calibration, which need not be done in the presence of the material to be tested. I further locate the flow-rate sensor upstream of the material to be tested. In operation, take both pressure and flow-rate readings directly from the respective sensors. These readings can be fed directly into an automatic recorder, which draws mechanically the output in the form of a graph, or may feed them to, for example, an integrating computer. Pore size characteristics then are computed and can be presented in a number of ways.

The siting of the flow-rate sensor upstream of the material to be tested is of great importance, since that sensor works at a higher pressure on that side of the test material than it would on the downstream side and furthermore the upstream positioning avoids any contamination of that sensor by the test liquid being swept from the material. In the ASTM method, a liquid trap is provided behind or downstream of the material, but will not prevent vapour and is not totally successful in preventing access of liquid into the subsequent stages of the apparatus, which therefore can affect the accuracy of the flow meter.

I further improve the process by standardising the test liquid. Those mentioned in the ASTM F 316-80 are water, petroleum distillate, de-natured alcohol or mineral oil. I find that various characteristics of volatility, surface tension or reactivity will not allow any one of those materials to be used over a wide range of materials to be tested. I have selected a liquid which is of the widest possible applicability, having very low surface tension and vapour pressure and in particular very low reactivity for the materials which are likely to form the materials under test. An example of such a liquid is known as Fluorinert (Registered Trade Mark), which is recommended by its makers Minnesota Mining and Manufacturing as a cooling liquid for electronic components and devices. The preferred Fluorinert liquid is known as FC43 having: a nominal boiling point of 174° C., a viscosity of 2.6 cs, a vapour pressure at 25° C. of 1.3 mmHg and a surface tension at the same temperature of 16 dynes per cm. Chemically, the liquid is a clear colourless perfluorocarbon fluid.

To relieve the operator further of the need for manual intervention, one may provide a motorised drive for the inlet flow regulator, whereby to achieve an increase of pressure applied to the sample at a pre-selected rate, which could be determined by the nature of the test material, but will usually be independent of it, at least within a certain ranges of pore sizes.

In my test method, it is preferred to take the wet curve first in a single sample holder and then repeat the run with the same sample in the same place to obtain the "dry" curve. In this way it is certain that an identical sample provides the two sets of data (a comparison between which gives the necessary data) and that no contamination or the like will enter the system as a result of its being opened up between the test. The ASTM method assumes that the dry test will be taken first, or else that two samples will be in the system.

The method of the invention may also include a calibration step performed before subjecting the sample to the test and which consists in running the gas through the system and calibrating the pressure detection system or scale of the recorder against a pressure gauge coupled into the line and then disconnecting the pressure input to the recorder and calibrating the flow-rate scale against a flow meter coupled into the line. The calibration may include the steps of returning the pressure and flow back to zero and recalibrating the zero of the recorder, for as often as is necessary. However, neither the pressure gauge nor the flow meter will be used in normal operation during running of the tests.

BRIEF DESCRIPTION OF THE DRAWINGS

FIG. 3 is a sketch perspective view of the apparatus of the invention as mounted for use.

DETAILED DESCRIPTION OF THE INVENTION

Figure 1:
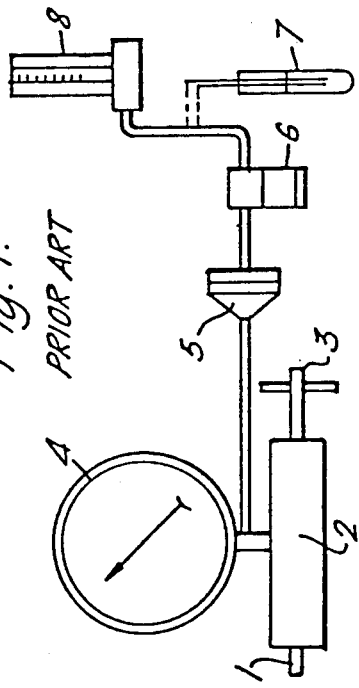
FIG. 1 is a diagrammatic view taken from ASTM F316-80 of the test apparatus as recommended and used until the present invention.

FIG. 1 shows a pressure source 1 with a pressure regulator 2 operated by a manual control 3. The pressure output from the regulator is seen on a gauge 4 and passes to a sample holder 5 between the two parts of which a sample is mounted, the sample having been moistened by any one of water, petroleum distillate, de-natured alcohol or mineral oil, all of a specified characteristics. Following the passage of gas through the sample is an oil trap 6 and the duct is initially coupled up after that to a so-called bubble point detector 7, wherein output if any being caused to bubble through liquid or to a rotameter 8 which is directly impelled by the flow of liquid. The initial breakthrough of gas through the sample is noted by operator observation of the bubble point detector who then sets a zero for a graph, which is then drawn by manual correlation of the pressure gauge against the flow rate downstream of the sample, as measured by the rotameter 8.

Figure 2:
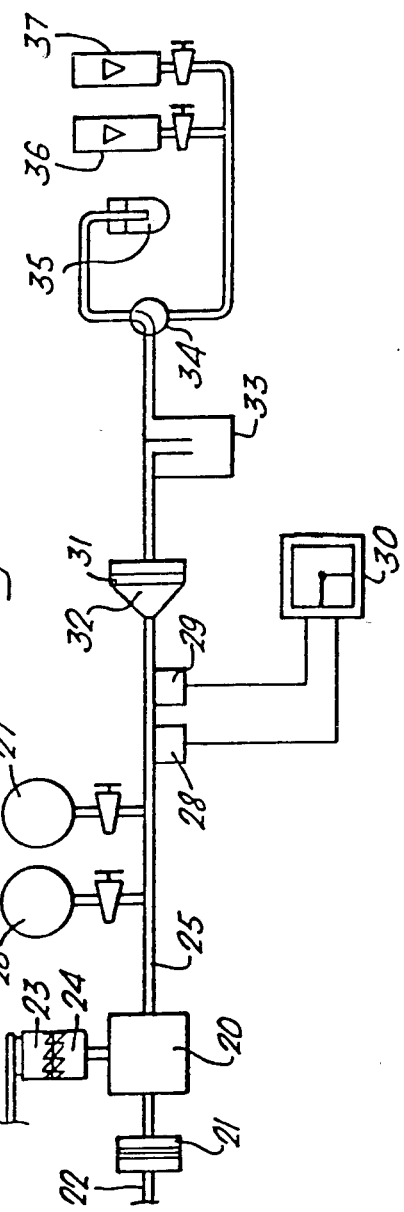
FIG. 2 is a similar diagram of the apparatus according to the present invention.

In the present invention in contrast, as seen in FIGS. 2 and 3, a pressure regulator 20, such as a Schrader regulator, preceded by a filter 21 between it and a source of compressed gas 22, usually compressed air is driven from a synchronous motor (not shown) through belting or other drive train and a ratchet clutch 23. The regulator can be returned to zero by manual intervention on a part 24 of the clutch nearer to the regulator, 20. Next, in the line 25 leading from the regulator are two pressure gauges 26,27 which can be brought into communication with the line through respective valves. The pressure gauges are used for calibration only and they are sensitive in different ranges of pressure, only one being used for any given calibration. Next in the line 25 are transducers 28,29 for pressure and flow-rate, respectively. The pressure transducer may be of any known type, but I have used one of the stressed metal film (also known as bonded foil strain gauge) type which gives an output to an X Y recorder 30 having a pen drivable over graph paper in either or both of the X Y directions in accordance with respective inputs. The other input is derived from a flow-rate transducer 29 and I prefer to use a thermal mass flow meter since it is devoid of moving parts. It can be seen that these devices are sensing both pressure and flow-rate in the line 25 upstream of the sample 31, which is mounted in a standard holder 32, and which optionally may be followed by the standard liquid trap 33 and by a two-way valve 34, which can divert flow either to a standard bubble point detector 35 or to standard flow meters 36,37. Which of these two flow meters is connected to the line is selected by respective valves. The flow meters 36,37, which are of the type which is impelled by the flow of gas, are used only in calibration of the device. The bubble point detector is however used to manually note the initial point of the breakthrough of the gas, at which time a tick or similar mark is made manually on the graph paper in the recorder 30 as a safeguard for extra accuracy in determining the origin of the curve which will be obtained.

In operation, calibration is first carried out without a sample in the holder. Gas is run through the system at a pressure similar to the maximum which will be expected to be used in the following test. One or other of the pressure gauges 26,27 is selected and the output from pressure transducer 28 only is fed to the recorder 30. The correlation between the position of the pen and the reading on the pressure gauges is made and if necessary the zeros are then calibrated, with recalibration at the high pressure and so on. Similarly, calibration of the flow-rate is carried out by taking the output from flow-rate transducer 29 only to the recorder and comparing the other reading of the pen with the reading achieved by one of the two direct-impelled flow meters 36 or 37 which may be appropriate to the expected maximum flow during the test. When calibration has been achieved the pressure gauges and the flow meters are switched out of the system.

Next, the valve 34 is switched over so that the bubble detector is in the circuit. A standard sample, which may be for example: a filter paper, a sintered micro-filter, a blotting paper, a geological material, or any other material of which it is wished to know the porosity, is saturated in Fluorinert FC43 and placed in the holder. The automatic drive 23 is coupled to the pressure regulator so there is an automatic and predetermined increase in the pressure applied to the sample and the test is run, achieving a wet curve graph. The test is continued until that graph line becomes substantially straight, showing substantially complete drying of the sample. The pressure is then returned to zero and the run repeated with the sample still in the holder to obtain the dry curve which is substantially a straight line. The two curves are plotted on the same piece of graph paper automatically by the recorder 30 and are then removed for the necessary interpretation.

It is apparent that once the output signals have been reduced to an electrical form as they are here, the results could be taken out to means such as a computer which would interpret them immediately in terms of for example pore size and distribution.

It can be seen that I have considerably improved and rendered more reliable the method and apparatus proposed in the ASTM F 316-80 by removing very largely the reliance on manual dexterity and skill, by changing and rearranging the components shown in that ASTM F 316-80 in order to improve the performance and reliability of the whole and by standardising the test liquid used to wet the material under test.

I claim:

1. A pore size characterizing device comprising: a gas pressure regulator arranged to be connected to receive a gas supply; a sample holder having an inlet and an outlet, said inlet being connected to said gas pressure regulator to receive gas therethrough, said sample holder being constructed to hold a sample pre-wetted with a liquid having characteristics of a perfluorocarbon, including a low surface tension and a low vapour pressure; a gas pressure sensor connected to said sample holder for measuring the differential pressure of gas across the sample; a gas flow sensor connected to measure the gas flow through the sample; and processing means responsive to said sensors for determining pore size characteristics of the sample.

2. A device according to claim 1, wherein the liquid used to pre-wet the sample is a perfluorocarbon.

3. A device according to claim 2, wherein the perfluorocarbon liquid has the physical and chemical properties of the liquid sold under the trademark Fluorinert ®.

4. A device according to claim 1 wherein the liquid used to pre-wet the sample has a low viscosity approximating 2.6 cs.

5. A device according to claim 1 wherein the liquid used to pre-wet the sample has a very low reactivity for the material under test.

6. A pore size characterizing device comprising: a gas pressure regulator arranged to be connected to receive a gas supply; a sample holder having an inlet and an outlet, said inlet being connected to said gas pressure regulator to receive gas therethrough, said gas pressure regulator being controlled to regulate the pressure of the gas supplied to the sample holder inlet in a predetermined manner, whereby to provide a known pressure of gas across the sample at a predetermined rate, said sample holder being constructed to hold a sample pre-wetted with a liquid having a low surface tension and a low vapour pressure; a gas pressure sensor connected to said sample holder for measuring the differential pressure of gas across the sample; a gas flow sensor connected to measure the gas flow through the sample; and processing means responsive to said sensors for determining pore size characteristics of the sample.

7. A device according to claim 6, wherein gas pressure gauge means is provided to calibrate the output from said gas pressure sensor.

8. A device according to claim 6, wherein gas flow metering means is provided to calibrate the output from said gas flow sensor.

9. A device according to claim 8, wherein said gas flow metering means is connected to the outlet of said sample holder.

10. A device according to claim 6, wherein said processing means includes a chart recorder.

11. A method of assessing pore size characteristics, comprising: first saturating a sample with a liquid having a low surface tension and a low vapour pressure, placing the sample in the sample holder of a device comprising: a gas pressure regulator arranged to be connected to receive a gas supply; a sample holder having an inlet and an outlet, said inlet being connected to said gas pressure regulator to receive gas therethrough, said sample holder being constructed to hold a sample pre-wetted with said liquid having a low surface tension and a low vapour pressure; a gas pressure sensor connected to said sample holder for measuring the differential pressure of gas across the sample; a gas flow sensor connected to measure the gas flow through the sample; and processing means responsive to said sensors for determining pore size characteristics of the sample; and increasing the pressure of gas supplied to said sample holder until the sample is substantially free of said liquid, then reducing the pressure to a lower value and increasing it again with the sample still in place.

12. A method according to claim 11, wherein the liquid used to saturate the sample is an inert perfluorocarbon fluid.

13. A method according to claim 12, wherein the liquid used has a boiling point of 174° C., a viscosity of 2.6 cs, a vapour pressure at 25° C. of a 1.3 mm Hg and a surface tension at 25° C. of 16 dynes per cm.

14. A method of assessing pore size characteristics, comrising: allowing gas to flow through a device in the absence of any sample; said device comprising: a gas pressure regulator arranged to be connected to receive a gas supply; a sample holder having an inlet and an outlet, said inlet being connected to said gas pressure regulator to receive gas therethrough, said sample holder being constructed to hold a sample pre-wetted with a liquid having a low surface tension and a low vapour pressure; a gas pressure sensor connected to said sample holder for measuring the differential pressure of gas across the sample; a gas flow sensor connected to measure the gas flow through the sample; gas flow metering means provided to calibrate the output from said gas flow sensor; gas pressure gauge means provided to calibrate the output from said gas pressure sensor; and processing means responsive to said sensors for determining pore size characteristics of the sample; said method further comprising: calibrating the output from said sensors using said pressure gauge means and said flow metering means, thereafter isolating said pressure gauge means and said metering means from the gas flow, reducing the gas flow to an initial value, placing a sample saturated in liquid having a low surface tension and a low vapour pressure in said sample holder, increasing the pressure of gas supplied to the sample holder until the sample is substantially free of said liquid, and then reducing the pressure to a lower value and increasing it again with the sample still in place.

15. A device according to claim 6, wherein at least one of said gas pressure sensor and said gas flow sensor is connected upstream of said sample holder.

* * * * *